(12) United States Patent
Strik et al.

(10) Patent No.: US 8,866,105 B2
(45) Date of Patent: Oct. 21, 2014

(54) SLEEVE HOLDER ASSEMBLY (75) Inventors: Joseph Strik, London (CA); Paul De Boer, London (CA)

(73) Assignee: Trojan Technologies (CA)

( * ) Notice: Subject to any disclaimer, the term of this patent is extended or adjusted under 35 U.S.C. 154(b) by 7 days.

(21) Appl. No.: 13/877,828

(22) PCT Filed: Oct. 3, 2011

(86) PCT No.: PCT/CA2011/001082
§ 371 (c)(1),
(2), (4) Date: Sep. 12, 2013

(87) PCT Pub. No.: WO2012/045148
PCT Pub. Date: Apr. 12, 2012

(65) Prior Publication Data
US 2014/0008547 A1    Jan. 9, 2014

Related U.S. Application Data (60) Provisional application No. 61/344,779, filed on Oct. 4, 2010.

(51) Int. Cl.
*A61L 2/10* (2006.01)
*C02F 1/32* (2006.01)

(52) U.S. Cl.
CPC . *A61L 2/10* (2013.01); *C02F 1/325* (2013.01); *C02F 2201/004* (2013.01)
USPC .......................................... 250/436

(58) Field of Classification Search
USPC ...................... 250/436, 435, 432 R
See application file for complete search history.

(56) References Cited

U.S. PATENT DOCUMENTS

| 5,019,256 | A * | 5/1991 | Ifill et al. ................ 210/232 |
| 6,039,460 | A | 3/2000 | Ng et al. |
| 7,741,617 | B2 | 6/2010 | Matthews et al. |
| 2004/0179977 | A1 | 9/2004 | Hargett, Jr. |

FOREIGN PATENT DOCUMENTS

| CA | 2311806 A1 | 10/1999 |
| CA | 2639952 A1 | 7/2006 |
| CN | 201110531 Y | 9/2008 |

OTHER PUBLICATIONS

International Search Report for International Application No. PCT/CA2011/001082 with a mailing date of Dec. 9, 2011.

* cited by examiner

*Primary Examiner* — Kiet T Nguyen
(74) *Attorney, Agent, or Firm* — Katten Muchin Rosenman LLP

(57) ABSTRACT

A sleeve holder assembly for a radiation source is disclosed. The sleeve holder assembly comprises: an elongate radiation transparent sleeve element; a sleeve holder receptacle portion coupled to the elongate radiation transparent sleeve element; a sleeve bolt assembly portion coupled to the sleeve holder receptacle portion; a first sealing element disposed between the sleeve holder receptacle portion and the sleeve bolt assembly portion; and a locking element configured to prevent decoupling of the sleeve bolt assembly portion and the sleeve holder receptacle portion. The first sealing element is configured to provide a substantially fluid impermeable seal between the elongate radiation transparent sleeve element and the sleeve holder receptacle portion.

29 Claims, 6 Drawing Sheets

SLEEVE HOLDER ASSEMBLY

CROSS-REFERENCE TO RELATED APPLICATION

The present application claims the benefit under 35 U.S.C. §119(e) of provisional patent application Ser. No. 61/344,779, filed Oct. 4, 2010, the contents of which are hereby incorporated by reference.

BACKGROUND OF THE INVENTION

1. Field of the Invention

In one of its aspects, the present invention relates to a sleeve holder assembly. In other of its aspects, the present invention relates to a radiation source assembly, a radiation source module and a fluid treatment system, each incorporating the sleeve holder assembly. Other aspects of the invention will become apparent to those of skill in the art upon reviewing the present specification.

2. Description of the Prior Art

Fluid treatment systems are known generally in the art.

For example, U.S. Pat. Nos. 4,482,809, 4,872,980 and 5,006,244 [all in the name of Maarschalkerweerd and hereinafter referred to as the Maarschalkerweerd Patents] all describe gravity fed fluid treatment systems which employ ultraviolet (UV) radiation.

Such systems include an array of UV lamp frames which include several UV lamps each of which are mounted within sleeves which extend between and are supported by a pair of legs which are attached to a cross-piece. The so-supported sleeves (containing the UV lamps) are immersed into a fluid to be treated which is then irradiated as required. The amount of radiation to which the fluid is exposed is determined by the proximity of the fluid to the lamps, the output wattage of the lamps and the fluid's flow rate past the lamps. Typically, one or more UV sensors may be employed to monitor the UV output of the lamps and the fluid level is typically controlled, to some extent, downstream of the treatment device by means of level gates or the like.

In recent years, there has been interest in the so-called "transverse-to-flow" fluid treatment systems. In these systems, the radiation source is disposed in the fluid to be treated in a manner such that the longitudinal axis of the radiation source is in a transverse (e.g., substantially orthogonal or vertical orientation of the radiation sources) relationship with respect to the direction of fluid flow past the radiation source. See, for example, any one of:

International Publication Number WO 2004/000735 [Traubenberg et al.];

International Publication Number WO 2008/055344 [Ma et al.];

International Publication Number WO 2008/019490 [Traubenberg et al.];

U.S. Pat. No. 7,408,174 [From et al.];

U.S. provisional patent application Ser. No. 61/193,686 [Penhale et al.], filed Dec. 16, 2008 (and corresponding to International Publication Number WO 2010/069072); and U.S. provisional patent application Ser. No. 61/202,576 [Penhale et al.], filed Mar. 13, 2009 (and corresponding to International Publication Number WO 2010/102383).

In the art, it is known to dispose the radiation source in a radiation transparent protective sleeve, typically made from quartz (the combination is commonly referred to as a radiation source assembly). This approach can involve the use of a sleeve holder assembly which is combination of plastic elements coupled to the radiation transparent protective sleeve. The plastic elements are typically in the form of a sleeve bolt or the like and it is this sleeve bolt which is mounted to the fluid treatment system to secure the radiation source assembly with respect to the fluid treatment system.

In typical use, the environment in which the radiation source assemblies are used is subject to temperature fluctuations. These temperature fluctuations can lead to cycles of expansion and shrinkage of the plastic components leading to loosening of the connection to the fluid treatment system which raises the risk of fluid leakage from the fluid treatment system to the outside environment. The primary reason for this is it is conventional to use O-ring seals or the like to prevent leakage of fluid from the fluid treatment system. While a prescribed compression ratio (or compressive force) may be applied to these O-ring seals when the radiation source assembly is initially installed in the fluid treatment system, the above-mentioned temperature fluctuations result in variation of this compression ratio (or compressive force)—for example, by loosening of the connection, which results in the potential for leakage of fluid from the fluid treatment system.

Accordingly, there remains a need in the art for a sleeve holder assembly which can be coupled to a fluid treatment system in a manner that reduces the likelihood of leakage of fluid from the fluid treatment system. It would be highly desirable to have such a sleeve holder assembly which could be relatively easily installed and removed from the fluid treatment system as desired for servicing and the like.

SUMMARY OF THE INVENTION

It is an object of the present invention to obviate or mitigate at least one of the above-mentioned disadvantages of the prior art.

It is another object of the present invention to provide a novel radiation source assembly.

It is another object of the present invention to provide a novel radiation source module.

It is another object of the present invention to provide a novel fluid treatment system.

Accordingly, in one of its aspects, the present invention provides a sleeve holder assembly for a radiation source, the sleeve holder assembly comprising:

an elongate radiation transparent sleeve element;

a sleeve holder receptacle portion coupled to the elongate radiation transparent sleeve element;

a sleeve bolt assembly portion coupled to the sleeve holder receptacle portion;

a first sealing element disposed between the sleeve holder receptacle portion and the sleeve bolt assembly portion, the first sealing element configured to provide a substantially fluid impermeable seal between the elongate radiation transparent sleeve element and the sleeve holder receptacle portion; and a locking element configured to prevent decoupling of the sleeve bolt assembly portion and the sleeve holder receptacle portion.

The invention also relates to a radiation source assembly, a radiation source module and to a fluid treatment system incorporating this sleeve holder assembly.

Thus, the present inventors have developed a novel sleeve holder assembly for a radiation source. The present sleeve holder assembly can be installed in a fluid treatment system with application of a prescribed compression ratio (or compressive force) on the sealing element. Advantageously, in the present sleeve holder assembly, the prescribed compression ratio (or compressive force) is subject to little or no variation as temperature around the sleeve holder assembly fluctuates up and down. Consequently, the potential for fluid leakage from the fluid treatment system is mitigated or obviated using the present sleeve holder assembly. In a particularly preferred embodiment of the sleeve holder assembly, a cap portion is provided which allows insertion of the radiation source in the sleeve holder assembly. When the radiation source is not installed in the sleeve holder assembly, in this preferred embodiment, the cap portion is biased closed thereby protecting the internals of the protective sleeve which prevents dust, grit, dirt and the like from entering the internal area of the sleeve holder assembly. When the radiation source is installed in the sleeve holder assembly, in the preferred embodiment, a tail section of the cap portion is engaged in a slot (or equivalent receptacle) in the fluid treatment system thereby further securing the sleeve holder assembly with respect to the fluid treatment system.

Other advantages of the invention will become apparent to those of skill in the art upon reviewing the present specification.

BRIEF DESCRIPTION OF THE DRAWINGS

Embodiments of the present invention will be described with reference to the accompanying drawings, wherein like reference numerals denote like parts, and in which.

DETAILED DESCRIPTION OF THE PREFERRED EMBODIMENTS

In one of its aspects, the present invention relates to a sleeve holder assembly for a radiation source, the sleeve holder assembly comprising: an elongate radiation transparent sleeve element; a sleeve holder receptacle portion coupled to the elongate radiation transparent sleeve element; a sleeve bolt assembly portion coupled to the sleeve holder receptacle portion; a first sealing element disposed between the sleeve holder receptacle portion and the sleeve bolt assembly portion, the first sealing element is configured to provide a substantially fluid impermeable seal between the elongate radiation transparent sleeve element and the sleeve holder receptacle portion; and a locking element configured to prevent decoupling of the sleeve bolt assembly portion and the sleeve holder receptacle portion. Preferred embodiments of this sleeve holder assembly may include any one or a combination of any two or more of any of the following features:

the sleeve holder receptacle portion comprises a first threaded portion and the sleeve bolt assembly comprises a second threaded portion configured to engage the first threaded portion;
the first sealing element is disposed distally with respect to the first threaded portion and the second threaded portion;
the locking element comprises a first locking portion disposed on the sleeve holder receptacle portion and a second locking portion disposed on the sleeve bolt assembly;
the first locking portion comprises a ratchet portion;
the ratchet portion comprises a plurality of tooth elements, each tooth element configured to engage the second locking portion disposed on the sleeve bolt assembly;
the ratchet portion comprises an annularly disposed plurality of tooth elements, each tooth element configured to engage the second locking portion disposed on the sleeve bolt assembly;
the plurality of tooth elements is configured to provide unidirectional engagement of the sleeve bolt assembly portion and the sleeve receptacle assembly portion;
the second locking portion comprises at least one locking ratchet tab;
the second locking portion comprises a plurality of locking ratchet tabs.
the second locking portion comprises a pair of locking ratchet tabs;
the second locking portion comprises a pair of locking ratchet tabs disposed substantially diametrically opposed to one another;
the locking element is disposed proximally with respect to the first sealing element;
the elongate radiation transparent sleeve element comprises a first diameter in a distal portion and a second diameter in a proximal portion, the first diameter and the second diameter being different;
the second diameter is larger than the first diameter;
the sleeve holder assembly further comprising a cushioning element disposed between the sleeve holder receptacle portion and the elongate radiation transparent sleeve element;
the cushioning element is disposed at a junction between the first diameter and the second diameter;
the first sealing element is resilient;
the first sealing element comprises an O-ring element;
the sleeve bolt assembly portion comprises a flange element configured to abut a proximal surface of the sleeve holder receptacle portion when the first sealing element is subjected to a prescribed compressive force;
the sleeve bolt assembly portion comprises a sleeve bolt locking element configured to secure the sleeve bolt assembly portion with respect to a fluid treatment system;
the sleeve bolt assembly portion comprises a sleeve bolt locking element configured to secure the sleeve bolt assembly portion with respect to a reactor lamp port element in a fluid treatment system;
the sleeve bolt assembly portion comprises a sleeve bolt locking element configured to secure the sleeve bolt assembly portion with respect to a a portion of a reactor lamp port element in a fluid treatment system;
the sleeve bolt assembly portion comprises a sleeve bolt locking element configured to secure the sleeve bolt assembly portion with respect to a receiving groove in a reactor lamp port element in a fluid treatment system;
the sleeve bolt assembly portion comprises a pair of sleeve bolt locking elements;
the sleeve bolt assembly portion comprises a pair of substantially diametrically opposed sleeve bolt locking elements;

the sleeve bolt locking elements have an asymmetric size configured to permit only a single correct position of the sleeve bolt assembly portion with respect to the fluid treatment system;

the sleeve bolt locking elements have an asymmetric shape configured to permit only a single correct position of the sleeve bolt assembly portion with respect to the fluid treatment system;

the sleeve bolt locking elements have an asymmetric size and an asymmetric shape configured to permit only a single correct position of the sleeve bolt assembly portion with respect to the fluid treatment system.

the sleeve bolt assembly portion comprises an opening for receiving the radiation source;

the sleeve bolt assembly portion comprises a cap portion configured to cover the opening when a radiation source is not present in the elongate radiation transparent sleeve element;

the sleeve bolt assembly portion comprises a cap portion configured to move between an open position to permit insertion of the radiation source in the opening and a closed position to cover the opening when a radiation source is not present in the elongate radiation transparent sleeve element;

the sleeve holder assembly further comprising a biasing element configured to urge the cap portion in the closed position when a radiation source is not present in the elongate radiation transparent sleeve element.

the cap portion is configured to pivot with respect to sleeve bolt assembly portion;

the cap portion comprises a first cap locking portion configured to secure the cap portion with respect to the sleeve bolt assembly portion when the cap portion covers the opening;

wherein the cap portion comprises a second cap locking portion to prevent rotation of the sleeve bolt assembly with respect to a fluid treatment system to which it is coupled when the radiation source is disposed in the elongate radiation transparent sleeve element;

the sleeve holder assembly further comprising a second sealing element disposed between the sleeve holder receptacle portion and the sleeve bolt assembly portion, the second sealing element being configured to provide a substantially fluid impermeable seal between the sleeve holder receptacle portion and the sleeve bolt assembly portion;

the second sealing element is disposed distally with respect to the first sealing element;

the second sealing element is disposed proximally with respect to the first sealing element;

the second sealing element is resilient;

the second sealing element comprises an O-ring element;

the elongate radiation transparent sleeve comprises a proximal open end and a distal closed end; and the protective sleeve is constructed of quartz.

Another aspect of the present invention relates to a radiation source assembly comprising the above and a radiation source disposed in the elongate radiation transparent sleeve element. Preferred embodiments of this radiation source assembly may include any one or a combination of any two or more of any of the following features:

the elongate radiation source is an ultraviolet radiation source;

the elongate radiation source is a low pressure ultraviolet radiation source;

the elongate radiation source is a low pressure, high output ultraviolet radiation source; and the elongate radiation source is medium pressure ultraviolet radiation source.

Another aspect of the present invention relates to a radiation source module comprising a support element for securing the module in a fluid treatment system and at least one radiation source assembly (preferably a plurality) as defined above. Preferably, the radiation source module comprises a plurality of radiation source assemblies secured to the support element.

Another aspect of the present invention relates to a fluid treatment system comprising a fluid treatment zone for receiving a flow of fluid and at least one radiation source module as described above, wherein the at least one radiation source module is configured such that the radiation source assembly is disposed in the fluid treatment zone. In an alternate embodiment, the fluid treatment system comprises a fluid treatment zone for receiving a flow of fluid and at least one reactor lamp port having coupled thereto the radiation source assembly described above disposed in the fluid treatment zone Preferred embodiments of either embodiment of this fluid treatment system may include any one or a combination of any two or more of any of the following features:

the fluid treatment zone is comprised in an open channel for receiving the flow of fluid;

the fluid treatment zone is comprised in a closed channel for receiving the flow of fluid;

the at least one radiation source assembly has a longitudinal axis disposed transverse to the direction of fluid flow through the fluid treatment zone;

the at least one radiation source assembly has a longitudinal axis disposed orthogonal to the direction of fluid flow through the fluid treatment zone; and the at least one radiation source assembly is disposed substantially vertically in the fluid treatment zone.

Figure 1:
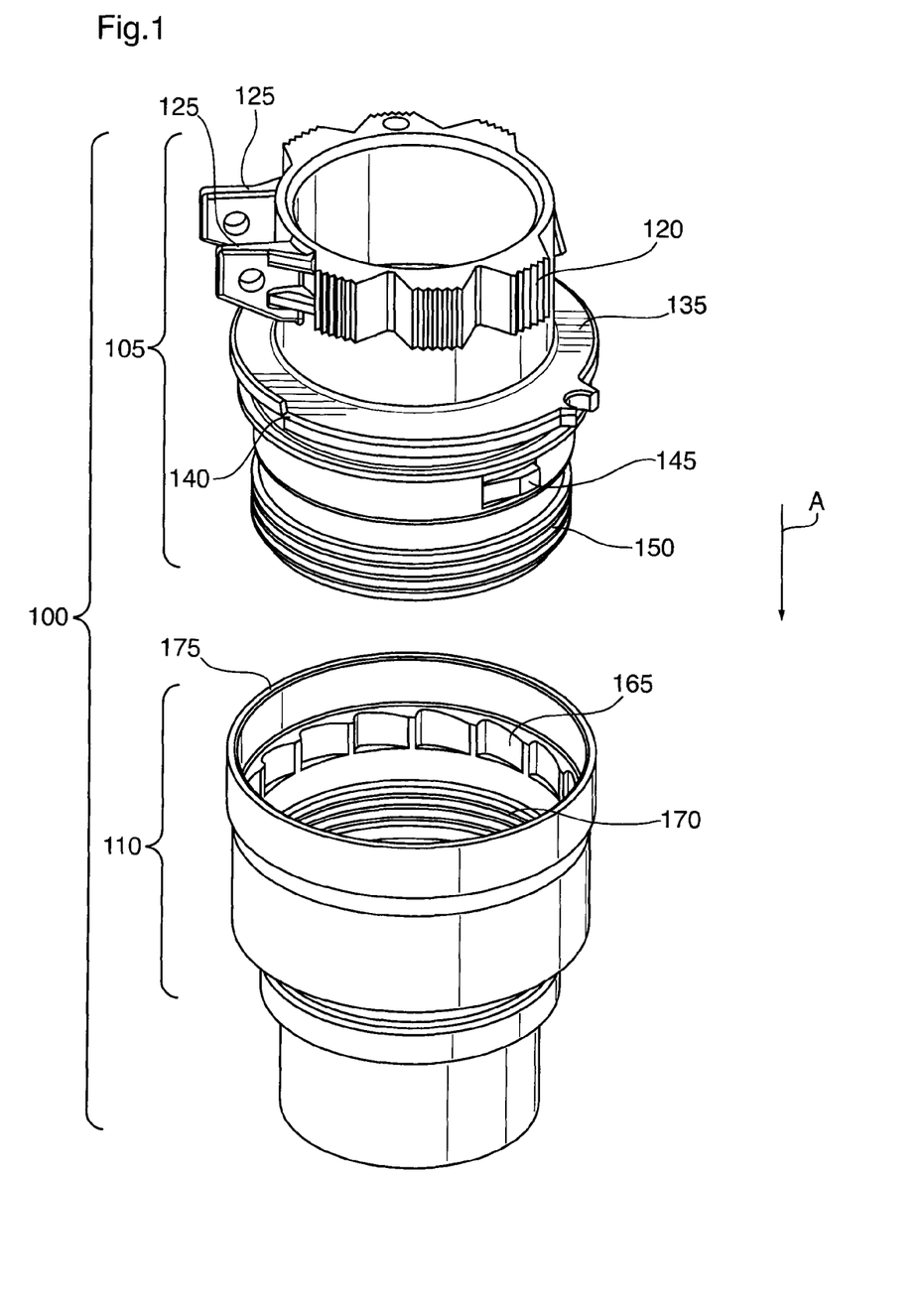
FIG. 1 illustrates an enlarged perspective view of a portion of a preferred embodiment of the present sleeve holder assembly in a disassembled state.
Figure 2:
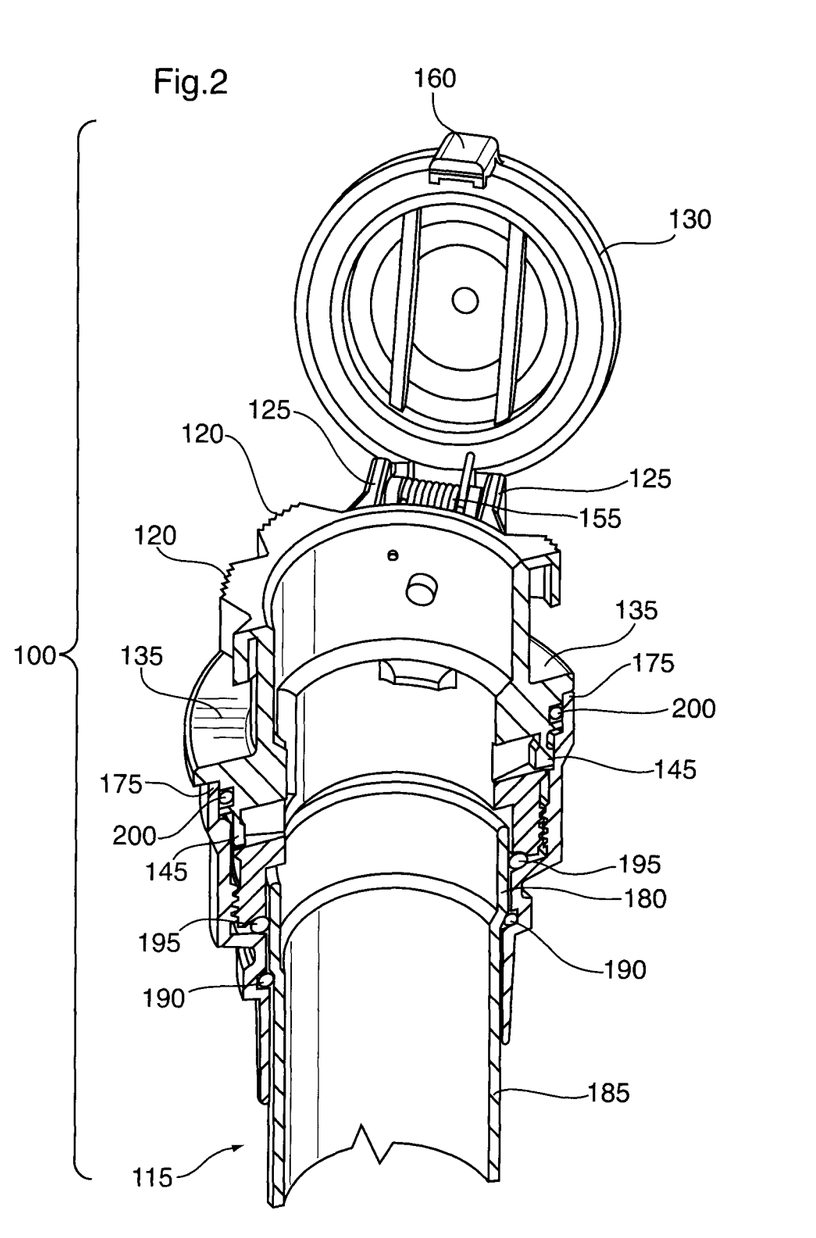
FIG. 2 illustrates a perspective view, in partial cross-section of a preferred embodiment of the present sleeve holder assembly.

With reference to FIGS. 1 and 2, there is illustrated a sleeve holder assembly 100. Sleeve holder assembly 100 comprises a sleeve bolt assembly 105, a sleeve holder receptacle 110 and an elongate radiation transparent sleeve 115 (only a portion of the elongate radiation transparent sleeve has been shown for clarity).

Sleeve bolt assembly 105 comprises a grip portion 120 and a pair of brackets 125 which support and are coupled to a cap portion 130 (cap portion 130 is not shown in FIG. 1 for clarity).

Sleeve bolt assembly 105 further comprises a flange portion 135 having a pair of asymmetric locking features 140 (only a single locking feature 140 is shown in FIG. 1 for clarity purposes). Sleeve bolt assembly 105 further comprises a pair of locking ratchet tabs 145 (again, for clarity only a single locking ratchet tab is shown in FIG. 1) and a threaded portion 150.

As shown particularly in FIG. 2, cap portion 130 is coupled to a spring element 155 disposed between support brackets 125. Cap portion 130 further comprises a locking clip 160.

Sleeve holder receptacle 110 comprises a one-way locking ratchet 165 in the form of plurality of tooth elements disposed annularly on an inner surface of sleeve holder receptacle 110. Also disposed in the interior surface of sleeve receptacle portion 110 is an threaded portion 170. An upper edge 175 of sleeve holder receptacle portion 110 has a diameter less than at least a portion of the diameter of flange portion 135 of sleeve bolt assembly 105.

Elongate radiation transparent sleeve element 115 comprises a proximal portion 180 having a larger diameter than a distal portion 185. Disposed at the junction between the proximal portion 180 and distal portion 185 of elongate radiation transparent sleeve element 115 is a cushioning element 190 which can be in the form of O-ring or the like.

Sleeve holder assembly 100 may be assembled in the following manner.

Sleeve bolt assembly 105 is inserted into sleeve holder receptacle 110 in the direction of arrow A (FIG. 1). Sleeve bolt assembly 105 is rotated such that threaded portion 150 of sleeve bolt assembly 105 engages with threaded portion 170 of sleeve holder receptacle portion 110. This rotation is continued until a prescribed compressive force is placed on a sealing element 195 disposed between a distal portion of sleeve bolt assembly 105 and an inner portion of sleeve holder receptacle 110—see FIG. 2. The prescribed compressive force may be selected by dimensioning sleeve bolt assembly 105 and sleeve holder receptacle 110 such that when edge 175 of sleeve holder receptacle portion 110 abuts against the underside of flange portion 135 of sleeve bolt assembly 105, a predetermined compressive force is applied to sealing element 195. This approach obviates or mitigates over-tightening of the components leading to possible breakage or other damage to sleeve holder assembly 100.

A second sealing element 200 is also disposed between sleeve bolt assembly portion 105 and sleeve holder receptacle 110 and provides supplementary sealing. The provision of sealing element 200 can be optional in some applications.

Importantly, as sleeve bolt assembly 105 is tightened with respect to sleeve holder receptacle 110, locking ratchet tabs 145 interact with locking ratchet 165 to lock the components together in a manner such that temperature fluctuations will not result in loosening of the connection. This is a particular advantage associated with the present sleeve holder assembly.

Figure 3:
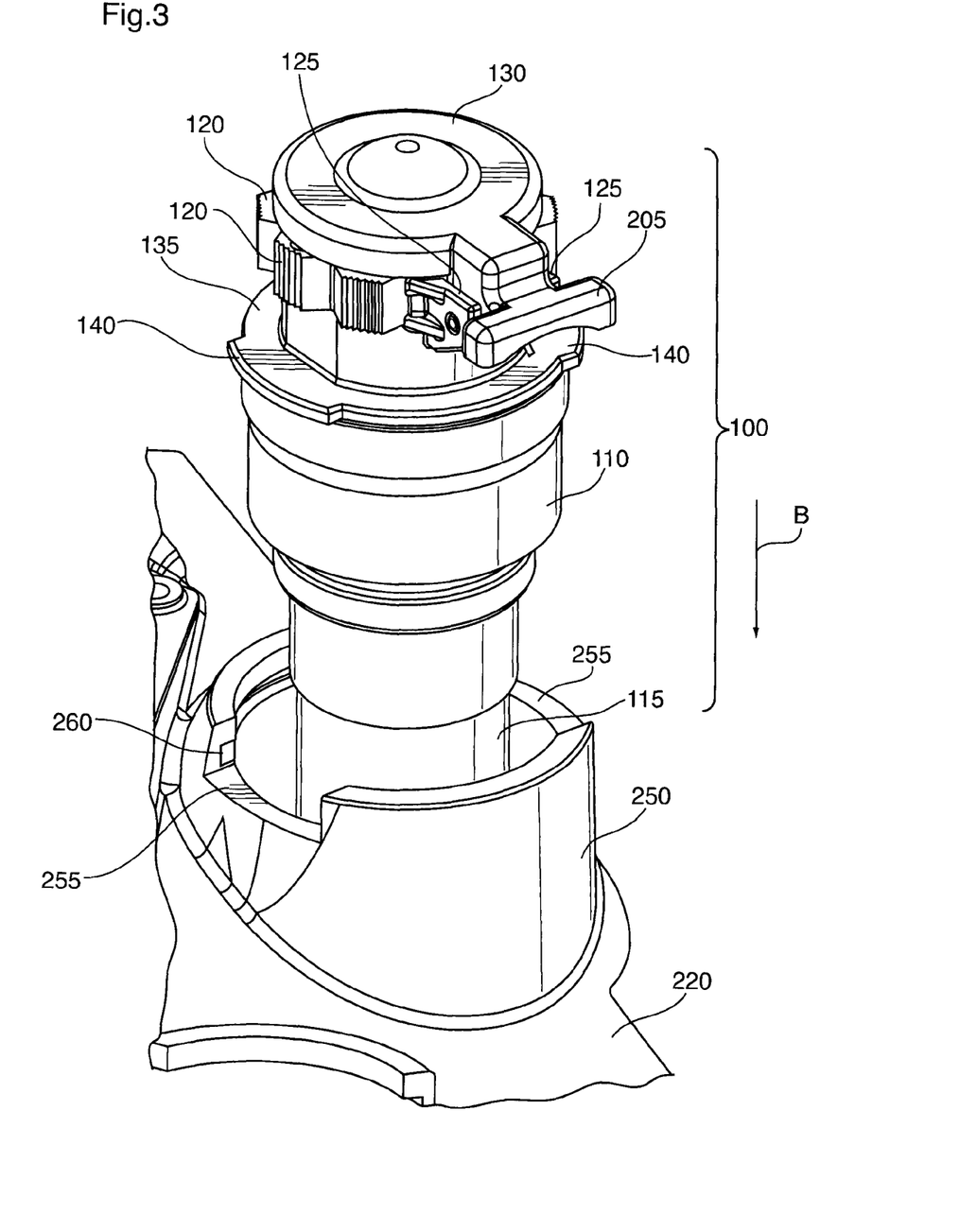
FIGS. 3 and 4 illustrate insertion of the present sleeve holder assembly in a fluid treatment system.
Figure 4:
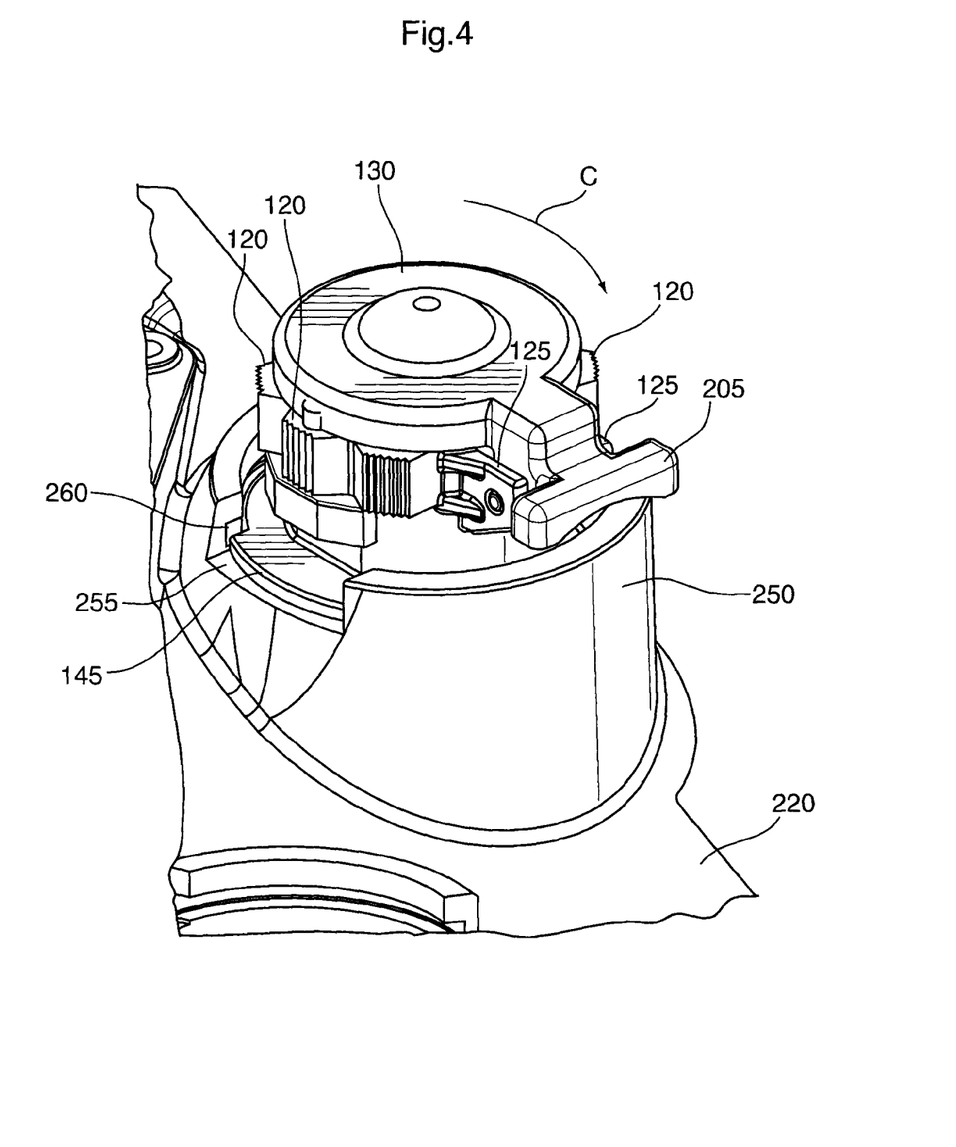
Figure 6:
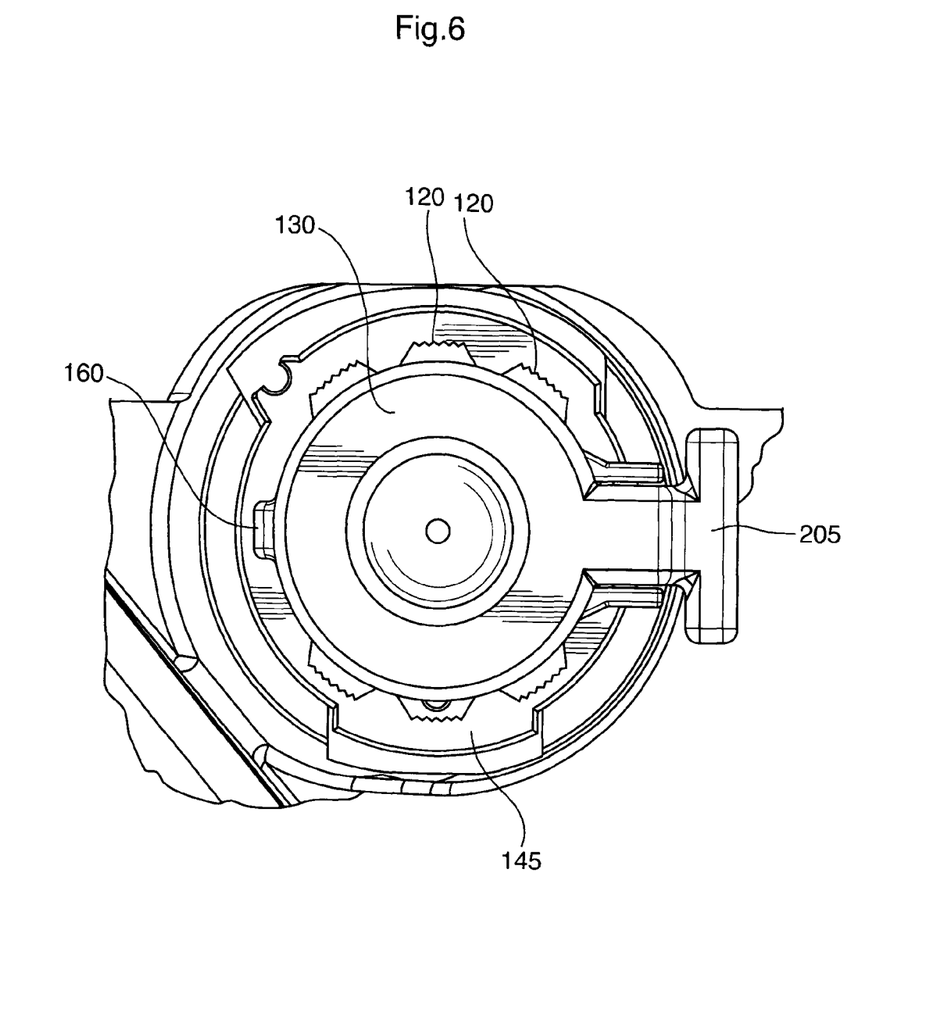
FIG. 6 illustrates a top view of the sleeve holder assembly illustrated in FIG. 4.

With particular reference to FIGS. 3-4 and 6, after assembly of sleeve holder assembly 100, it may be inserted in a reactor lamp port 250 in a fluid treatment system 220. As shown, reactor lamp port 250 comprises a pair of slots 255 which are dimensioned to receive locking features 140 on sleeve bolt assembly 105. Also disposed in reactor lamp port 250 are a pair of grooves 260 which are dimensioned to receive locking features 140 disposed on sleeve bolt assembly 105. Preferably, locking features 140 have an asymmetric shape and/or an asymmetric size so that sleeve holder assembly 100 can only be inserted in single correct position in reactor lamp port 250.

Thus, with reference to FIG. 3, sleeve holder assembly 100 is lowered into lamp reactor port 250 in the direction of arrow B. With reference to FIGS. 4 and 6, once locking features 140 of sleeve bolt assembly 105 are aligned with grooves 260 of reactor lamp port 250, sleeve holder assembly 100 is rotated in the direction of arrow C thereby locking it in place with respect to reactor lamp port 250.

Figure 5:
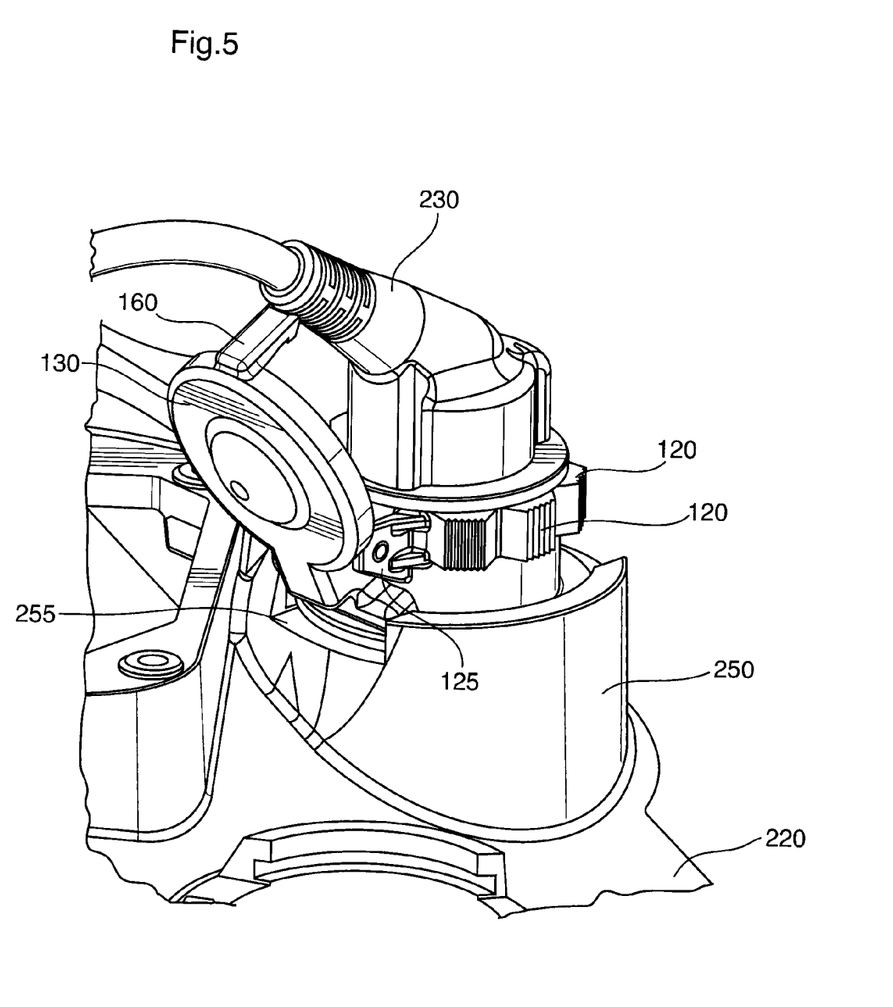
FIG. 5 illustrates a perspective view of the sleeve holder assembly illustrated in FIG. 2 installed in a fluid treatment system and connected to a source of electrical power.

With reference to FIG. 5, when it is desired to install a radiation source into sleeve holder assembly 100, locking clip 160 of cap portion 130 is actuated to allow cap portion 130 to be swung open thereby exposing the internal portion of sleeve holder assembly 100. Next, a radiation source (not shown for clarity) is inserted into sleeve holder assembly 100 and coupled to an electrical connection 230.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. A sleeve holder assembly for a radiation source, the sleeve holder assembly comprising:
    an elongate radiation transparent sleeve element;
    a sleeve holder receptacle portion coupled to the elongate radiation transparent sleeve element;
    a sleeve bolt assembly portion coupled to the sleeve holder receptacle portion;
    a first sealing element disposed between the sleeve holder receptacle portion and the sleeve bolt assembly portion, the first sealing element configured to provide a substantially fluid impermeable seal between the elongate radiation transparent sleeve element and the sleeve holder receptacle portion; and
    a locking element configured to prevent decoupling of the sleeve bolt assembly portion and the sleeve holder receptacle portion.

2. The sleeve holder assembly defined in claim 1, wherein the sleeve holder receptacle portion comprises a first threaded portion and the sleeve bolt assembly comprises a second threaded portion configured to engage the first threaded portion.

3. The sleeve holder assembly defined in claim 2, wherein the first sealing element is disposed distally with respect to the first threaded portion and the second threaded portion.

4. The sleeve holder assembly defined in claim 1, wherein the locking element comprises a first locking portion disposed on the sleeve holder receptacle portion and a second locking portion disposed on the sleeve bolt assembly.

5. The sleeve holder assembly defined in claim 4, wherein the first locking portion comprises a ratchet portion.

6. The sleeve holder assembly defined in claim 4, wherein the second locking portion comprises a plurality of locking ratchet tabs.

7. The sleeve holder assembly defined in claim 1, wherein the elongate radiation transparent sleeve element comprises a first diameter in a distal portion and a second diameter in a proximal portion, the first diameter and the second diameter being different.

8. The sleeve holder assembly defined in claim 7, wherein the second diameter is larger than the first diameter.

9. The sleeve holder assembly defined in claim 1, wherein the sleeve bolt assembly portion comprises a flange element configured to abut a proximal surface of the sleeve holder receptacle portion when the first sealing element is subjected to a prescribed compressive force.

10. The sleeve holder assembly defined in claim 1, wherein the sleeve bolt assembly portion comprises a sleeve bolt locking element configured to secure the sleeve bolt assembly portion with respect to a fluid treatment system.

11. The sleeve holder assembly defined in claim 10, wherein the sleeve bolt locking elements have an asymmetric size and an asymmetric shape configured to permit only a single correct position of the sleeve bolt assembly portion with respect to the fluid treatment system.

12. The sleeve holder assembly defined in claim 1, wherein the sleeve bolt assembly portion comprises an opening for receiving the radiation source.

13. The sleeve holder assembly defined in claim 12, wherein the sleeve bolt assembly portion comprises a cap portion configured to move between an open position to permit insertion of the radiation source in the opening and a closed position to cover the opening when a radiation source is not present in the elongate radiation transparent sleeve element.

14. The sleeve holder assembly defined in claim 13, further comprising a biasing element configured to urge the cap portion in the closed position when a radiation source is not present in the elongate radiation transparent sleeve element.

15. The sleeve holder assembly defined in claim 13, wherein the cap portion comprises a first cap locking portion configured to secure the cap portion with respect to the sleeve bolt assembly portion when the cap portion covers the opening.

16. The sleeve holder assembly defined in claim 15, wherein the cap portion comprises a second cap locking portion to prevent rotation of the sleeve bolt assembly with respect to a fluid treatment system to which it is coupled when the radiation source is disposed in the elongate radiation transparent sleeve element.

17. The sleeve holder assembly defined in claim 1, further comprising a second sealing element disposed between the sleeve holder receptacle portion and the sleeve bolt assembly portion, the second sealing element being configured to provide a substantially fluid impermeable seal between the sleeve holder receptacle portion and the sleeve bolt assembly portion.

18. The sleeve holder assembly defined in claim 17, wherein the second sealing element is disposed distally with respect to the first sealing element.

19. A radiation source assembly comprising the sleeve holder assembly defined in claim 1 and a radiation source disposed in the elongate radiation transparent sleeve element.

20. The radiation source assembly defined in claim 19, wherein the elongate radiation source is an ultraviolet radiation source.

21. A radiation source module comprising a support element for securing the module in a fluid treatment system and at least one radiation source assembly defined in claim 19 secured to the support element.

22. The radiation source module defined in claim 21 comprising a plurality of radiation source assemblies secured to the support element.

23. A fluid treatment system comprising a fluid treatment zone for receiving a flow of fluid and at least one radiation source module defined in claim 21, wherein the at least one radiation source module is configured such that the radiation source assembly is disposed in the fluid treatment zone.

24. The fluid treatment system defined in claim 23, wherein the fluid treatment zone is comprised in an open channel for receiving the flow of fluid.

25. The fluid treatment system defined in claim 23, wherein the fluid treatment zone is comprised in a closed channel for receiving the flow of fluid.

26. The fluid treatment system defined in claim 23, wherein the at least one radiation source assembly has a longitudinal axis disposed transverse to the direction of fluid flow through the fluid treatment zone.

27. The fluid treatment system defined in claim 23, wherein the at least one radiation source assembly has a longitudinal axis disposed orthogonal to the direction of fluid flow through the fluid treatment zone.

28. The fluid treatment system defined in claim 23, wherein the at least one radiation source assembly is disposed substantially vertically in the fluid treatment zone.

29. A fluid treatment system comprising a fluid treatment zone for receiving a flow of fluid and at least one reactor lamp port having coupled thereto the radiation source assembly defined in claim 19 disposed in the fluid treatment zone.

* * * * *